US012773171B2

(12) United States Patent
Huang et al.

(10) Patent No.: US 12,773,171 B2
(45) Date of Patent: Oct. 27, 2026

(54) SYSTEMS AND METHODS FOR PREDICTIVE GLUCOSE MANAGEMENT

(71) Applicant: The Board of Trustees of the Leland Stanford Junior University, Stanford, CA (US)

(72) Inventors: Yuhao Huang, Stanford, CA (US); Casey Halpern, Philadelphia, PA (US); Jonathon Parker, Scottsdale, AZ (US); Rajat Shivacharan, Germantown, MD (US); Jeffrey B. Wang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 201 days.

(21) Appl. No.: 18/574,287

(22) PCT Filed: Aug. 30, 2022

(86) PCT No.: PCT/US2022/075695
§ 371 (c)(1),
(2) Date: Dec. 26, 2023

(87) PCT Pub. No.: WO2023/034820
PCT Pub. Date: Mar. 9, 2023

(65) Prior Publication Data

US 2024/0293088 A1 Sep. 5, 2024

Related U.S. Application Data

(60) Provisional application No. 63/238,583, filed on Aug. 30, 2021.

(51) Int. Cl.
*A61B 5/00* (2006.01)
*A61B 5/145* (2006.01)

(52) U.S. Cl.
CPC ........ *A61B 5/7278* (2013.01); *A61B 5/14532* (2013.01); *A61B 5/4064* (2013.01);
(Continued)

(58) Field of Classification Search
CPC . A61B 5/7278; A61B 5/14532; A61B 5/4064; A61B 5/4839; A61B 5/7221;
(Continued)

(56) References Cited

U.S. PATENT DOCUMENTS 5,198,977 A * 3/1993 Salb .................... A61B 5/0042 382/128
5,797,853 A * 8/1998 Musha .................. A61B 5/369 600/545

(Continued)

FOREIGN PATENT DOCUMENTS

CN 103959291 B 5/2018
CN 117794455 A 3/2024

(Continued)

OTHER PUBLICATIONS

Extended European Search Report for European Application No. 22865742.5, Search completed Dec. 14, 2024, Mailed Jan. 7, 2025, 08 Pgs.

(Continued)

*Primary Examiner* — May A Abouelela
(74) *Attorney, Agent, or Firm* — KPPB LLP

(57) ABSTRACT

Systems and methods for predictive glucose in accordance with embodiments of the invention are illustrated. One embodiment includes glucose management device, including a brain signal recorder, and a controller, including a processor, and a memory, the memory containing a glucose monitoring application configured to direct the processor to record a brain activity signal of a user's brain using the brain
(Continued)

signal recorder, and decode the brain activity signal to predict future glucose levels of the patient.

20 Claims, 4 Drawing Sheets

(52) U.S. Cl.
CPC .......... *A61B 5/4839* (2013.01); *A61B 5/7221* (2013.01); *A61B 5/7275* (2013.01); *A61B 5/746* (2013.01)

(58) Field of Classification Search
CPC ....... A61B 5/7275; A61B 5/746; A61B 5/245; A61B 5/37; A61B 5/4836; A61B 5/372; A61B 5/7267; A61B 5/7282; G16H 40/63; G16H 40/67; G16H 50/20; G16H 50/70; G16H 20/17
See application file for complete search history.

(56) References Cited

U.S. PATENT DOCUMENTS 6,572,542 B1 * 6/2003 Houben ................. G16H 50/20 128/920
7,727,147 B1 * 6/2010 Osorio .............. A61M 5/14244 600/347
8,118,741 B2 2/2012 Beck-Nielsen
8,201,330 B1 6/2012 Rood et al.
8,577,440 B2 11/2013 Afanasewicz et al.
8,628,472 B2 1/2014 Beck-Nielsen
8,870,766 B2 10/2014 Stivoric et al.
9,585,607 B2 3/2017 Kamath et al.
10,178,952 B2 * 1/2019 Westermann .......... A61B 5/374
10,327,656 B2 6/2019 Madsen et al.
10,716,896 B2 * 7/2020 O'Connor ......... A61M 5/14248
10,827,956 B2 11/2020 Brister et al.
10,998,101 B1 * 5/2021 Tran ....................... G16H 20/60
11,020,035 B2 6/2021 Dudek et al.
11,064,917 B2 7/2021 Simpson et al.
11,229,406 B2 1/2022 Zhong et al.
11,445,974 B2 9/2022 Jensen et al.
11,672,422 B2 6/2023 Brister et al.
11,744,943 B2 9/2023 Dobbles et al.
11,857,764 B2 * 1/2024 Harris ................. A61M 5/1723
11,963,801 B2 * 4/2024 Budiman ............... A61B 5/742
12,161,842 B2 * 12/2024 Ulrich .................... G16H 20/17
12,318,577 B2 * 6/2025 Mazlish .............. A61M 5/1723
2008/0243022 A1 10/2008 Donnett et al.
2008/0306353 A1 12/2008 Douglas et al.
2010/0058480 A1 * 3/2010 Hedberg ................ A61B 5/318 705/50
2011/0054264 A1 * 3/2011 Fischell ................. G16H 40/67 600/300
2011/0082711 A1 * 4/2011 Poeze .................. A61B 5/6825 600/300
2012/0029336 A1 2/2012 Terada et al.
2012/0302858 A1 11/2012 Kidmose et al.
2013/0018249 A1 1/2013 Storm
2013/0198685 A1 * 8/2013 Bernini ................. G06F 3/0484 715/800
2013/0204152 A1 * 8/2013 Roth .................. A61B 5/14532 600/544
2013/0274580 A1 10/2013 Madsen et al.
2014/0012511 A1 1/2014 Mensinger et al.
2014/0032194 A1 * 1/2014 Albisser ................. G16H 15/00 703/11
2014/0073892 A1 3/2014 Randloev et al.
2014/0371802 A1 12/2014 Mashiach et al.
2015/0038806 A1 * 2/2015 Kaleal, III ........... A61B 5/4833 600/301
2015/0141763 A1 * 5/2015 Roth .................... A61B 5/1455 600/301
2015/0257645 A1 * 9/2015 Bae ....................... G06F 1/3203 340/870.07
2015/0313498 A1 11/2015 Coleman et al.
2015/0366518 A1 * 12/2015 Sampson ............. A61B 5/7264 600/509
2016/0030670 A1 * 2/2016 Fischl ................. A61M 5/1723 604/504
2016/0081623 A1 3/2016 Lunner
2016/0213261 A1 * 7/2016 Fleischer ............. A61B 5/0205
2016/0256086 A1 9/2016 Byrd et al.
2016/0256629 A1 9/2016 Grosman et al.
2016/0354039 A1 * 12/2016 Soto ......................... A61B 5/74
2016/0367202 A1 12/2016 Carter et al.
2017/0067846 A1 * 3/2017 Schaible ............. A61M 5/1723
2017/0156662 A1 * 6/2017 Goodall ................. A61N 2/002
2017/0164876 A1 * 6/2017 Hyde .................... A61B 5/1118
2017/0164878 A1 * 6/2017 Connor .................. G09B 19/00
2017/0164893 A1 * 6/2017 Narayan .............. A61B 5/4836
2017/0173262 A1 6/2017 Veltz
2017/0185284 A1 6/2017 Bhavaraju et al.
2017/0215759 A1 8/2017 Dudek et al.
2017/0216524 A1 * 8/2017 Haider .............. A61M 5/14248
2017/0251967 A1 * 9/2017 Premsukh ............ A61B 5/0004
2017/0259072 A1 * 9/2017 Newham ............ A61N 1/37276
2018/0042513 A1 * 2/2018 Connor .................. A61B 5/369
2018/0103859 A1 * 4/2018 Provenzano ......... A61B 5/0024
2018/0271455 A1 9/2018 Zhong et al.
2018/0353112 A1 12/2018 Dassau et al.
2019/0000350 A1 * 1/2019 Narayan ................ G16H 50/50
2019/0159705 A1 5/2019 Sim et al.
2019/0223747 A1 7/2019 Chou
2019/0231254 A1 * 8/2019 Mosebach ............ A61B 5/4809
2019/0231255 A1 * 8/2019 Mosebach ............ A61B 5/7282
2019/0246982 A1 8/2019 Mackellar et al.
2019/0247650 A1 * 8/2019 Tran ................... A61N 1/36003
2019/0252079 A1 8/2019 Constantin et al.
2020/0000406 A1 * 1/2020 Saidi ...................... H04R 25/00
2020/0121199 A1 * 4/2020 Freeman .............. A61B 5/4875
2020/0138300 A1 5/2020 Fleischer et al.
2020/0268260 A1 8/2020 Tran
2020/0297256 A1 9/2020 Seo
2020/0375549 A1 12/2020 Wexler et al.
2020/0376271 A1 * 12/2020 Barrera .................. A61B 5/388
2021/0038897 A1 2/2021 Molnar et al.
2021/0100952 A1 * 4/2021 Brown .............. A61M 5/14244
2021/0228134 A1 7/2021 Trapero Martin et al.
2021/0233637 A1 * 7/2021 Georgiou ............... G16H 20/17
2021/0241916 A1 8/2021 Wexler et al.
2021/0272696 A1 * 9/2021 DeMazumder ........ G16H 15/00
2021/0290111 A1 * 9/2021 Liu .................... A61B 5/14532
2022/0039699 A1 2/2022 Esenaliev
2022/0061728 A1 3/2022 Goldstein
2022/0117503 A1 4/2022 Wang et al.
2022/0233773 A1 * 7/2022 Rueda ............... A61M 5/14248
2022/0253686 A1 8/2022 Cui et al.
2022/0265178 A1 8/2022 Tran
2022/0313172 A1 10/2022 Nie et al.
2022/0338792 A1 10/2022 Elwood et al.
2023/0169648 A1 * 6/2023 Kasai ................... A61B 5/4088 382/128
2023/0225659 A1 7/2023 Azemi et al.
2023/0298754 A1 * 9/2023 Bitetti .................... G16H 20/30 705/2
2024/0299669 A1 * 9/2024 Sjolund .................. A61B 5/746
2025/0221673 A1 7/2025 Huang et al.

FOREIGN PATENT DOCUMENTS

CN 113144394 B * 1/2025 ......... A61B 5/14553
EP 1827209 B1 10/2016
EP 3150121 B1 10/2018
EP 3708080 A1 9/2020
EP 4346595 A1 4/2024
JP 2024532089 A 9/2024
WO WO-2017205734 A1 * 11/2017 ............ A61B 5/352
WO 2023034820 A1 3/2023

OTHER PUBLICATIONS

International Preliminary Report on Patentability for International Application PCT/US2022/075695, Report issued Mar. 5, 2024, Mailed on Mar. 14, 2024, 05 Pgs.

(56) References Cited

OTHER PUBLICATIONS

International Search Report and Written Opinion for International Application No. PCT/US2022/075695, Search completed Nov. 14, 2022, Mailed Dec. 19, 2022, 15 Pgs.
Ngo et al., "Electroencephalogram Spectral Moments for the Detection of Nocturnal Hypoglycemia", IEEE Journal of Biomedical and Health Informatics, IEEE, Piscataway, NJ, USA, Jul. 29, 2019, vol. 24, No. 5, pp. 1237-1245, XP011786353, ISSN: 2168-2194, DOI: 10.1109/JBHI.2019.2931782.
Kistenmacher et al., "Persistent Blood Glucose Reduction upon Repeated Transcranial Electric Stimulation in Men", Brain Stimulation, 2017, vol. 10, Issue 4, pp. 780-786, doi:10.1016/j.brs.2017.03.011.

* cited by examiner

SYSTEMS AND METHODS FOR PREDICTIVE GLUCOSE MANAGEMENT

CROSS-REFERENCE TO RELATED APPLICATIONS

The current application is a national stage application of PCT Application No. PCT/US2022/075695 entitled "Systems and Methods for Predictive Glucose Management" filed Aug. 30, 2022, which claims the benefit of and priority under 35 U.S.C. § 119(e) to U.S. Provisional Patent Application No. 63/238,583 entitled "Systems, Methods, and Composition of Decoding Glucose Using Brain Activity" filed Aug. 30, 2021. The disclosures of PCT Patent Application No. PCT/US2022/075695 and U.S. Provisional Patent Application No. 63/238,583 are hereby incorporated by reference in their entirety for all purposes.

FIELD OF THE INVENTION

The present invention generally relates to the prediction of future glucose levels in a patient based on brain activity, and preemptive management based on said prediction.

BACKGROUND

Glucose is a simple sugar that is a critical energy source for all known life. Glucose levels are typically split into two different measurements. Blood glucose is a measurement of glucose in blood and is generally measured as the venous plasma level, where it tends to be 3-5 mg/mL less than in arterial blood because some of the glucose diffuses from the plasma to interstitial fluid as blood circulates through the capillary system. Interstitial glucose, in contrast, is a measurement of glucose in the interstitial fluid of the body. Interstitial glucose and blood glucose measurements often substantially differ even if measured at the same time.

Hyperglycemia is a medical condition in which the patient has an excessive amount of glucose in the blood plasma. This typically refers to a blood glucose reading of higher than 200 mg/dL. Diabetes is a group of metabolic disorders in which the patient has hyperglycemia over a prolonged period of time. Severe complications can arise during prolonged or extreme hyperglycemia. Diabetes is due to the pancreas not producing enough insulin, or the cells of the body not properly responding to insulin. Hypoglycemia is the converse medical condition in which the patient has too little glucose in the blood plasma which can be buffered by physiologic changes, but in severe cases can result in coma, seizures, and even death.

Continuous Glucose Monitors (CGMs) are small sensors that are inserted under the skin that periodically measure interstitial glucose levels. CGMs can record data and store it, as well as produce alarms if dangerous interstitial glucose levels are detected. Typically, CGMs are used in conjunction with fingerstick blood tests to guide patient treatment decisions.

Brain activity refers to action potentials occurring in the brain. Brain activity can be recorded using a wide array of different measurement techniques which all produce different views on brain activity. For example, electroencephalograms (EEGs) use electrode sensors on the scalp to record electrical signals in the brain in a lower resolution fashion compared to brain activity recorded via an electrocorticogram (ECOG) which uses electrode sensors implanted into or on the surface of the brain. Further still, electrodes implanted into the brain may have even higher spatial resolution of the thousands and tens of thousands of neurons (local field potentials) or order of single or small groups of neurons (so called single or multi-unit records). Microelectrode arrays or single electrodes can be implanted into the brain structures to record individual action potentials (or "spikes") in a particular region of interest.

SUMMARY OF THE INVENTION

Systems and methods for predictive glucose in accordance with embodiments of the invention are illustrated. One embodiment includes glucose management device, including a brain signal recorder, and a controller, including a processor, and a memory, the memory containing a glucose monitoring application configured to direct the processor to record a brain activity signal of a user's brain using the brain signal recorder, and decode the brain activity signal to predict future glucose levels of the patient.

In another embodiment, the glucose monitoring application further directs the processor to provide a warning when estimated glucose levels rise above a threshold value.

In a further embodiment, the brain signal recorder is: an electroencephalography (EEG) device; a functional near-infrared spectroscopy (fNIRS) device; an electrocorticography (ECOG) device; a deep-brain stimulation device; and a magnetoencephalography (MEG) device.

In still another embodiment, to decode the brain activity signal, the glucose monitoring application further directs the processor to provide the brain activity signal to a multivariate decoder trained on spectral profiles of intracranial activity.

In a still further embodiment, the brain activity signal describes the spectral profile of the broadband brain activity.

In yet another embodiment, the glucose monitoring application further directs the processor to deliver a therapy to the user based on predicted future glucose levels in order to manage glucose levels in a desired therapeutic range.

In a yet further embodiment, the therapy is insulin provided via an insulin pump to the user.

In another additional embodiment, the therapy is brain stimulation.

In a further additional embodiment, the glucose monitoring application further directs the processor to store the predicted future glucose level in the memory, and validate the predicted future glucose level based on a measured glucose level received from a glucose monitor.

In another embodiment again, the glucose level is selected from the group consisting of: blood glucose level; and interstitial glucose level.

In a further embodiment again, A method of managing glucose levels, including recording a brain activity signal of a user's brain using a brain signal recorder, and decoding the brain activity signal to predict future glucose levels of the patient.

In still yet another embodiment, the method further includes providing a warning when estimated glucose levels rise above a threshold value.

In a still yet further embodiment, the brain signal recorder is selected from the group consisting of: an electroencephalography (EEG) device; a functional near-infrared spectroscopy (fNIRS) device; an electrocorticography (ECOG) device; a deep-brain stimulation device; and a magnetoencephalography (MEG) device.

In still another additional embodiment, the method further includes decoding the brain activity signal comprises providing the brain activity signal to a multivariate decoder trained on spectral profiles of intracranial activity.

In a still further additional embodiment, the brain activity signal describes the spectral profile of the broadband brain activity.

In still another embodiment again, the method further includes delivering a therapy to the user based on predicted future glucose levels in order to manage glucose levels in a desired therapeutic range.

In a still further embodiment again, the therapy is insulin provided via an insulin pump to the user.

In yet another additional embodiment, the therapy is brain stimulation.

In a yet further additional embodiment, the method further includes storing the predicted future glucose level in the memory, and validating the predicted future glucose level based on a measured glucose level received from a glucose monitor.

In yet another embodiment again, the glucose level is selected from the group consisting of: blood glucose level; and interstitial glucose level.

In still yet another embodiment again, a system for predictively managing glucose levels including a brain activity recorder, a glucose monitor, an insulin pump, and a controller, where the controller is configured to record brain activity of a user using the brain activity recorder, predict a future hyperglycemic state of the patient based on the recorded brain activity, and direct the insulin pump to deliver insulin to avoid the predicted hyperglycemic state.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
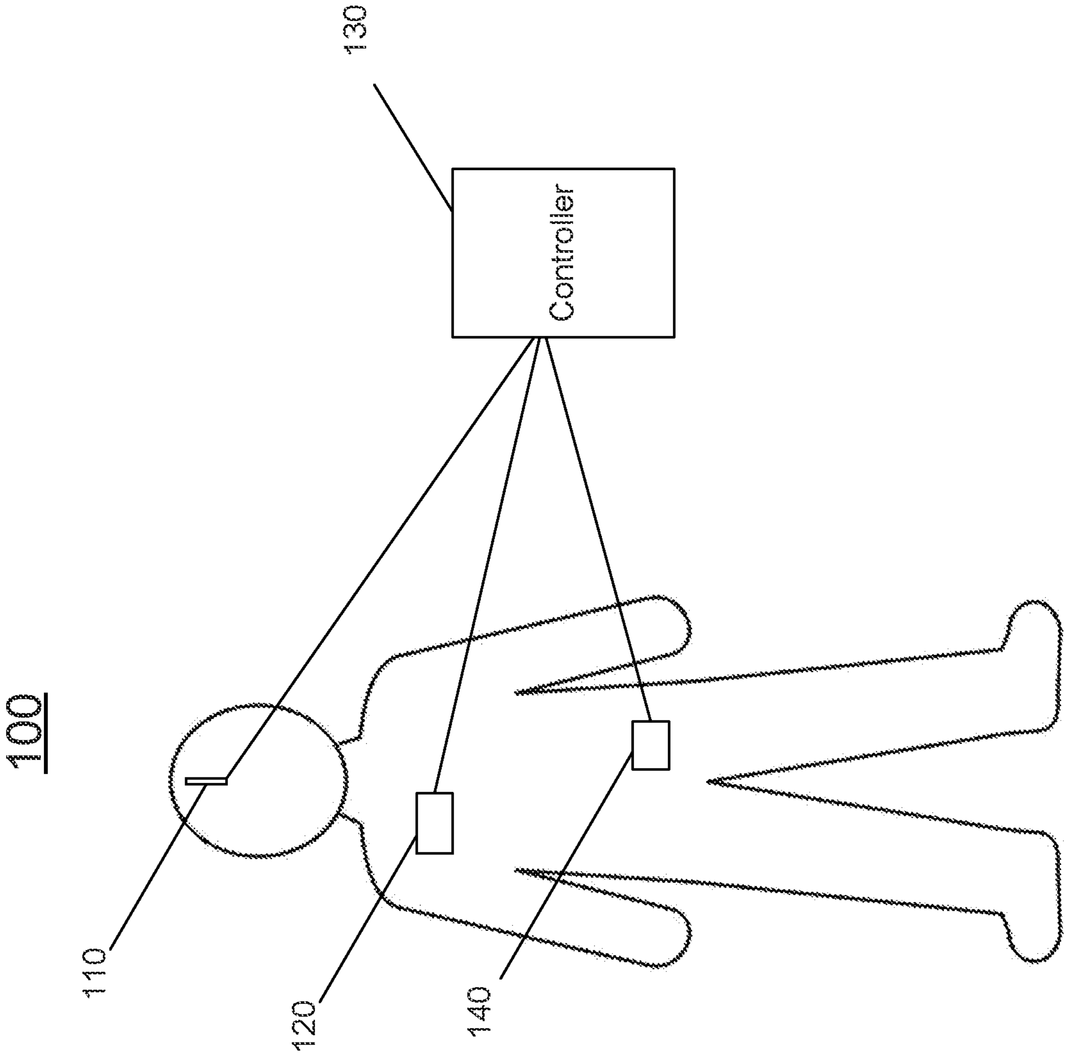
FIG. 1 illustrates a predictive glucose management system in accordance with an embodiment of the invention.

Metabolic syndromes and diabetes are increasingly prevalent health conditions, now affecting a broader range of ages in our global population. Specifically, the significant morbidity and mortality associated with diabetes have created a major toll on the healthcare system, including extensive costs, both personal and societal, in the form of medical expenditures for the disease itself and loss of workforce productivity from disability associated with disease progression. Hence, the ability to prevent development of diabetes and its subsequent complications is a high-impact area of public health for intervention. Additionally, eating behavior and physiologic regulation of the body's metabolic and weight balance entails a complex interplay of hormonal signaling and behaviors. In this context, close monitoring and control of blood glucose levels has been shown to be one of the best and most reliable methods to prevent complications of both hypo- and hyperglycemia.

Controlling blood glucose is important beyond the scope of diabetes, as both hyper- and hypoglycemia in hospitalized and critically-ill patients are associated with increased cost, length of stay, morbidity, and morality. Patients, especially those in intensive care units may suffer from stress-related hyperglycemia as a result of severe injuries and illnesses, e.g. traumatic brain injury (TBI), intracranial hemorrhage, stroke, subarachnoid hemorrhage (SAH), and many others. Conservative glycemic control has been associated with better outcomes in these patients.

Current iterations of continuous glucose monitors (CGMs) rely on interstitial glucose measurements as a proxy for blood glucose levels, which have an intrinsic lag time and are subject to interference by medications and extreme blood glucose values. Conventional CGMs are also unable to anticipate abnormal glucose levels; as a reactive modality, they can only respond to hypo or hyperglycemia once the abnormality has already occurred. In addition, patients with severe disease may have chronically elevated glucose levels that are refractory to conventional treatment options including continuous insulin infusion. Systems and methods described herein seek to rectify these limitations by predicting what a patient's glucose levels will be in the next several hours. Using this information, preemptive treatment can be delivered to the patient in order to avoid deleterious glucose levels from occurring.

In many embodiments, predictive glucose management (PGM) systems and methods described herein decode brain activity in order to predict the patient's future glucose levels. In a variety of embodiments, brain activity is measured using a non-invasive modality such as electroencephalography (EEG), functional near-infrared spectroscopy (fNIRS), magnetoencephalography (MEG), or any other modality as appropriate to the requirements of specific applications of embodiments of the invention. However, brain activity can be recorded using intracranial sensors if available, such as (but not limited to) deep brain stimulation (DBS) systems, or ECOG. In various embodiments, PGM systems are wearable or otherwise minimally invasive with respect to a patient's life outside of a clinical setting.

In numerous embodiments, systems and methods described herein involve closed-loop management of glucose levels, where preemptive treatment is provided to the patient to avoid hyper- or hypo-glycemia. For example, patients may be delivered long-acting insulin, an insulin analogue, and/or any other hyperglycemia control drug as appropriate to the requirements of specific applications of embodiments of the invention in anticipation of future glucose changes. By way of further example, brain stimulation may be provided in order to perturb the glucose encoding network in the brain in order to alter blood glucose levels for the subsequent several hours. Brain stimulation may be provided by an already implanted DBS electrode depending on implantation location, any other type of implanted electrode, or via a non-invasive brain stimulation modality such as (but not limited to) transcranial magnetic stimulation (TMS), transcranial direct current stimulation (tDCS), transcranial focused ultrasound (tFUS), and/or any other modality as appropriate to the requirements of specific applications of embodiments of the invention. In various embodiments, brain stimulation modalities may be utilized as an adjunct to insulin when the patient is refractory to standard treatments. PGM system architectures are discussed in further detail below.

Predictive Glucose Management Systems

PGM systems record and decode brain activity to estimate likely glucose levels of a patient in the next several hours. Typically, the predictions are accurate out for at least 2-8 hours, although depending on the patient and condition, this number may increase. In many embodiments, PGM systems provide these predictions to the patient and/or medical professionals. However, in various embodiments, PGM systems are further capable of closed-loop glucose level control by continuously predicting future glucose levels and altering treatment (e.g. drug delivery rate, brain stimulation, etc.) to avoid the predicted deleterious change in glucose level. In this way, PGMs can perform as an artificial pancreas system with superior glucose management capabilities. In some embodiments, patient and/or medical professional authorization is required before treatment is delivered and/or modified by the PGM.

Turning now to FIG. 1, an example PGM system architecture in accordance with an embodiment of the invention is illustrated. PGM system 100 includes a brain activity recorder 110. In the illustrated embodiment, brain activity recorder 110 is a deep brain stimulation system. However, as can readily be appreciated, any brain activity recorder can be used, including those that are non-invasive as discussed above. In some embodiments, the brain activity recorder is a wearable device, rather than an implanted device. PGM system 100 further includes a CGM 120. In many embodiments CGMs are used to continuously confirm the accuracy interstitial blood glucose predictions, and may further act as a redundant warning modality. However, CGMs may not be present in all PGM systems as appropriate to the requirements of specific applications of embodiments of the invention.

A controller 130 is communicatively coupled with the brain activity recorder 110, the CGM 120, and an insulin infusion pump 140. In many embodiments, the communication between different components may not be direct. For example, a brain activity recorder may provide data to a CGM which in turn is provided to the controller rather than communicating with the controller directly. Indeed, as one of ordinary skill in the art would appreciate, any communications architecture can be used without departing from the scope or spirit of the invention.

In numerous embodiments, controllers process recorded brain activity to generate predictions regarding the patient's glucose levels. Controllers may provide predictions for only one of interstitial or blood glucose levels. In some embodiments both interstitial and blood glucose level predictions are computed. Further, controllers may be implemented using any of a variety of computing platforms. In various embodiments, the controller is a smart phone, a smart watch, a tablet computer, a personal computer, and/or any other personal wearable device. In some embodiments, the controller may be integrated into a medical device or a medical server system, e.g. a hospital computer network, or cloud medical system.

In various embodiments, insulin infusion pumps can variably infuse insulin as dictated by the controller. Further, other drugs rather than insulin may be provided via a similar infusion pump depending on the needs of the patient. As can be readily appreciated, many PGM systems may not include any infusion pumps if drug delivery is unadvisable for the particular patient. Similarly, PGMs may further include methods for delivering brain stimulation as an alternative treatment. In various embodiments, the brain activity recorder may also function as a brain stimulation device. Indeed, any number of different PGM system architectures can be used depending on the needs of a specific patient as appropriate to the requirements of specific applications of embodiments of the invention.

Figure 2:
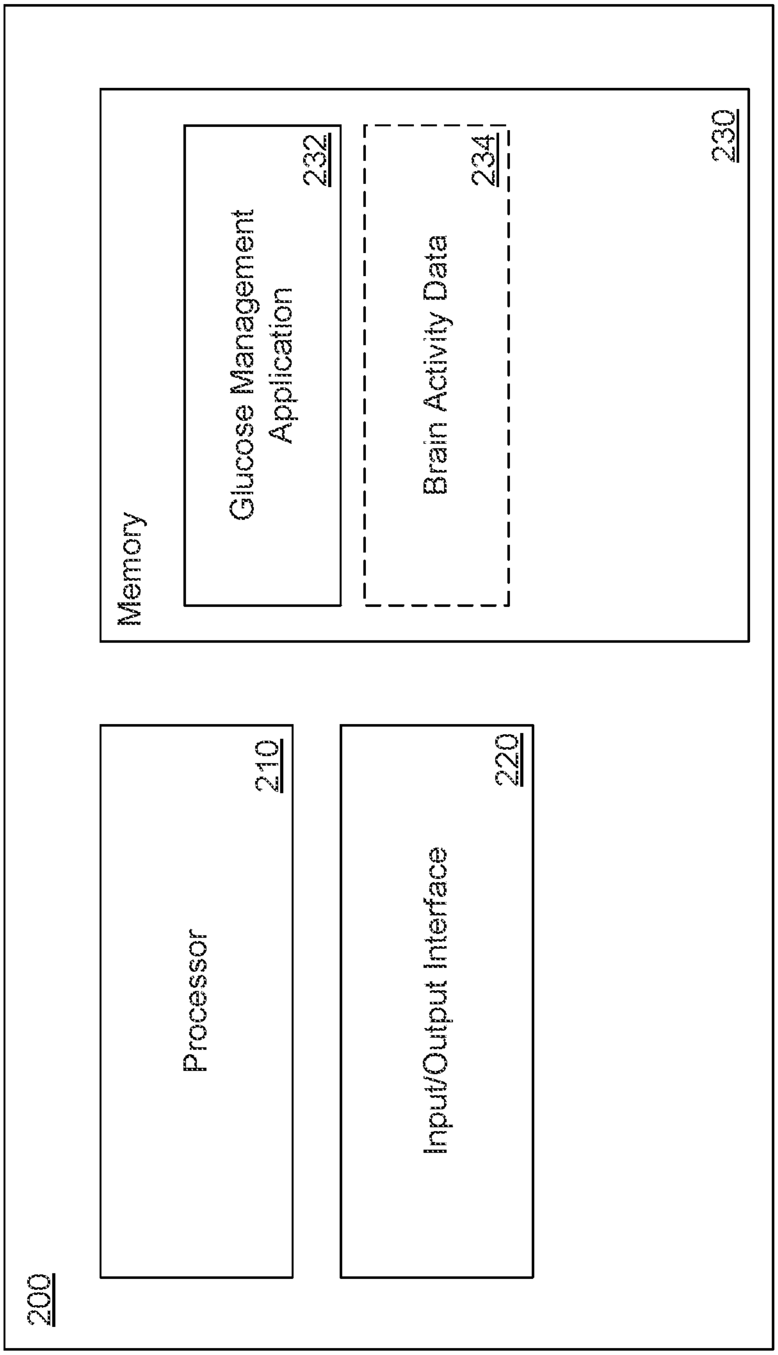
FIG. 2 illustrates a block diagram for a controller in accordance with an embodiment of the invention.

Turning now to FIG. 2, a block diagram for a controller in accordance with an embodiment of the invention is illustrated. Controller 200 includes a processor 210. In many embodiments, the processor is a logic circuit capable of executing instructions such as (but not limited to) a central processing unit (CPU), a graphics processing unit (GPU), a field programmable gate array (FPGA), an application-specific integrated circuit (ASIC), and/or any combination thereof. In many embodiments, more than one processor can be used. The controller 200 further includes an input/output (I/O) interface 220. The I/O interface can be used to communicate with different PGM system components and/or $3^{rd}$ party components such as (but not limited to) displays, speakers, CGMs, brain activity recorders, stimulation devices, infusion pumps, cellphones, medical devices, computers, and/or any other component via wired or wireless connections.

The controller 200 further includes a memory 230. The memory 230 can be made of volatile memory, nonvolatile memory, or any combination thereof. The memory 230 contains a glucose management application 232. The glucose management application can direct the processor to carry out various PGM processes as described herein. In many embodiments, the memory 230 further contains brain activity data obtained from brain activity recorders. Brain activity data can describe brain activity as a signal or set of signals. In some embodiments, brain activity data includes waveforms recorded by sensor electrodes. In various embodiments, one or more waveforms are recorded for each electrode ("channel"). In a number of embodiments, the brain activity data describes the spectral profile of broadband brain activity. In a variety of embodiments, the glucose management application configures the processor to act as a multivariate decoder for brain activity data. As can be readily appreciated, controllers can be manufactured in different ways using similar computing components without departing from the scope or spirit of the invention. PGM processes are discussed in further detail below.

Predictive Glucose Management

PGM processes involve the collection and use of brain activity to predict future glucose levels of a patient. In numerous embodiments, treatment recommendations or the treatments themselves can be triggered by a prediction of hyper- or hypoglycemia in order to stabilize the glucose levels at a healthier range. Peripheral glucose levels tend to largely follow circadian dynamics and are strongly coherent to intracranial high frequency activity (HFA, 70-170 Hz) across multiple brain regions. As such, whole brain activity can be used in the predictive modeling process. In some embodiments, brain activity data from known glucose-sensors such as the hypothalamus, amygdala, and hippocampus are used instead of or in conjunction with brain activity from other regions and/or the whole brain.

In order to process data coming from one or more brain activity recorders, a machine learning model can be trained. In some embodiments, the training process is performed using data acquired from the patient on which the trained model will be used. In various embodiments, the model can be pre-trained on standardized data and training can be completed using patient data. In various embodiments, the model is continuously refined using predictions and subsequent validation as measured using a CGM. While linear models are often considered to be less predictive than more modern machine learning models, in many embodiments a linear model is sufficient for accurate prediction. However, in various embodiments, more complex predictive machine learning models can be used, such as (but not limited to) other types of regression models, neural networks, and others as appropriate to the requirements of specific applications of embodiments of the invention.

Figure 3:
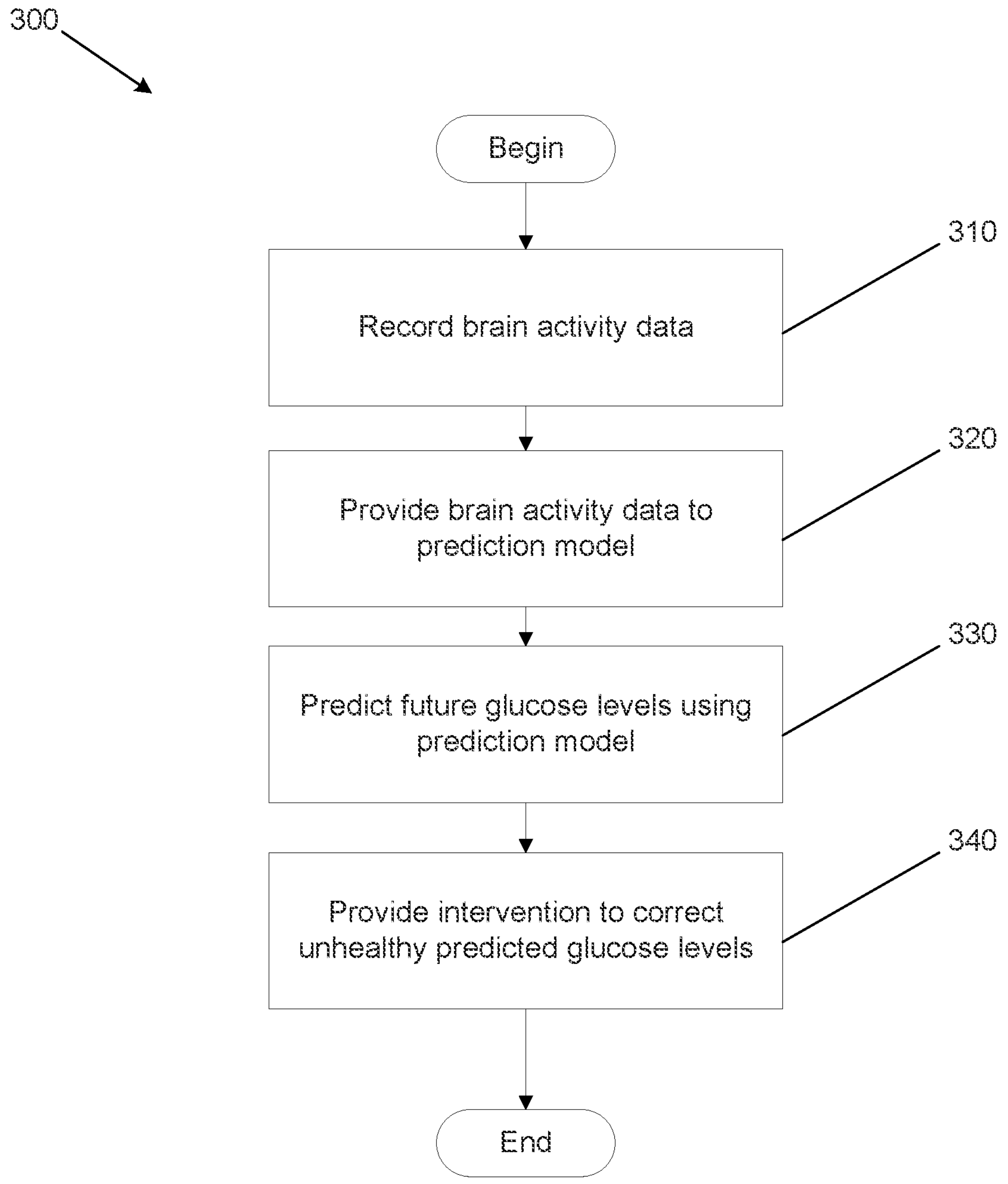
FIG. 3 is a flow chart for a process for managing glucose levels in accordance with an embodiment of the invention.

Turning now to FIG. 3, a flow chart for a PGM process for predictively managing glucose levels in accordance with an embodiment of the invention is illustrated. Process 300 includes recording (310) brain activity using a brain activity recorder, and providing (320) the brain activity data to a trained prediction model. The prediction model predicts (330) future glucose levels. In many embodiments, the certainty of the prediction may decrease the further in the future the prediction is made. In various embodiments, multiple predictions are provided at different time points, and only those above a predetermined confidence threshold as determined by a medical professional are used. In some embodiments, a hard limit is set on how far ahead the predictions are made for. If a hypo- and/or hyperglycemic state is predicted, a medical intervention is provided (340) to avoid the unhealthy dip or spike, respectively, in glucose levels. In various embodiments, the medical intervention is automatically provided, e.g. via control of an infusion pump and/or via brain stimulation. In various embodiments, a warning is provided to the patient and/or medical professional that an unhealthy glucose level is predicted. In some embodiments, confirmation is required before the medical intervention is provided.

While a particular process is illustrated in FIG. 3, as can readily be appreciated, various modifications can be made without departing from the scope or spirit of the invention. For example, pre-recorded brain activity data can be provided and used to make predictions. Further, interventions need not be recommended nor provided in all cases. In many situations, it is beneficial to merely have a warning.

Figure 4:
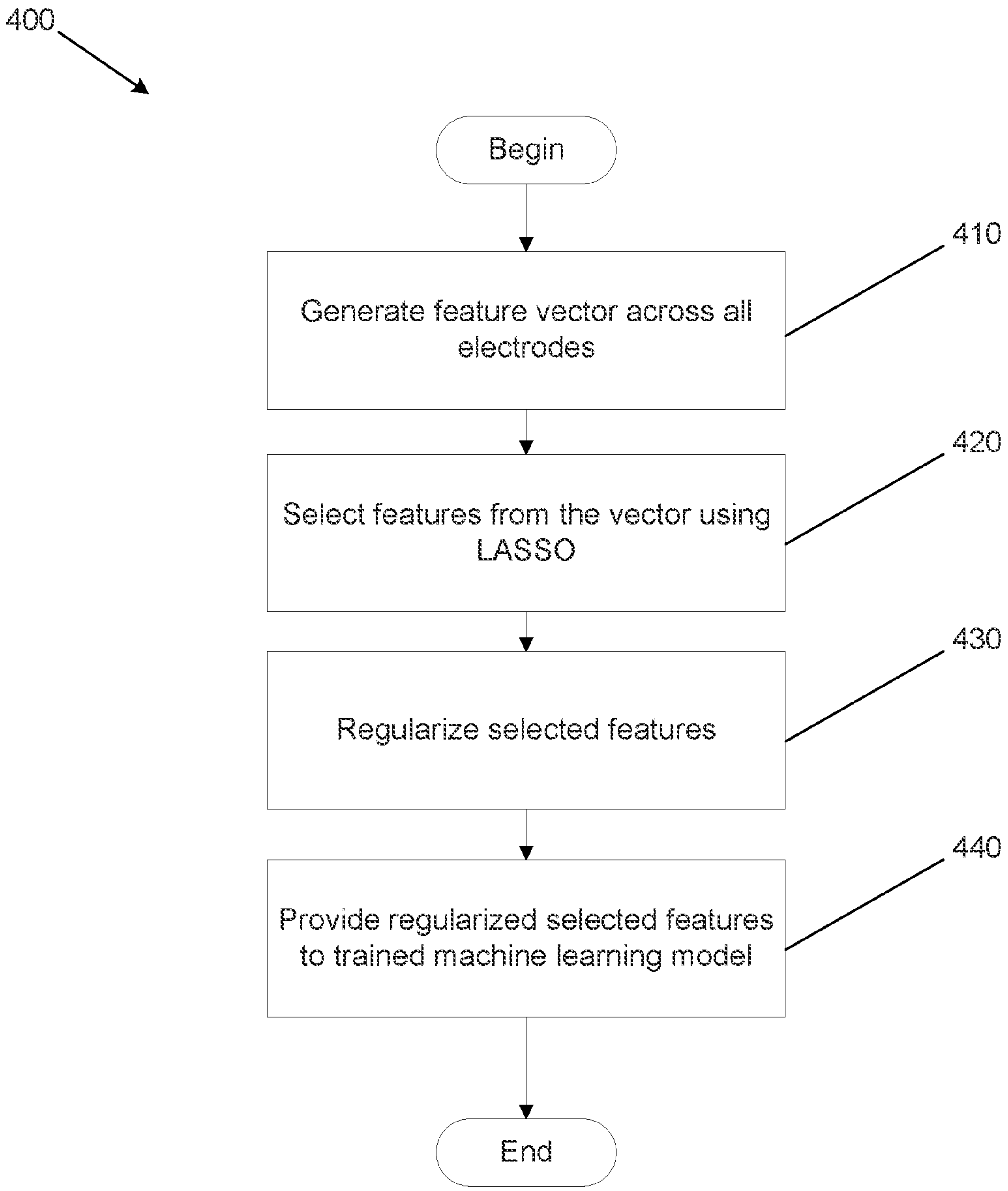
FIG. 4 is a flow chart for a process for predicting glucose levels in accordance with an embodiment of the invention.

Turning now to FIG. 4, a flow chart of a PGM process for predicting glucose levels based on brain activity data in accordance with an embodiment of the invention is illustrated. Process 400 includes generating (410) a feature vector across all electrode (or sensor) channels. In numerous embodiments, all frequency bands across all channels are flattened into a single feature vector. A Least absolute shrinkage and selection operator (LASSO) model is used to select (420) a subset of features from the feature vector for regularization (430). The regularized features are provided (440) to the trained machine learning model to produce one or more predictions. In numerous embodiments, a similar process is used to train the model using labeled training data from the patient and/or other patients. While specific machine learning models are discussed herein, many different machine learning models can be used without departing from the scope or spirit of the invention.

Although specific methods of PGM are discussed above, many different methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A glucose management device, comprising: a brain signal recorder; and a controller, comprising:
a processor; and
a memory, the memory containing a glucose monitoring application configured to direct the processor to:
record a brain activity signal of a user's brain using the brain signal recorder; and
decode the brain activity signal to predict future glucose levels of the user, wherein the brain activity signal is coherent to intracranial high frequency activity, and wherein the predicted future glucose levels comprise glucose levels predicted at least two hours in advance.

2. The glucose management device of claim 1, wherein the glucose monitoring application further directs the processor to provide a warning when estimated glucose levels rise above a threshold value.

3. The glucose management device of claim 1, wherein the brain signal recorder is selected from the group consisting of: an electroencephalography (EEG) device; a functional near-infrared spectroscopy (fNIRS) device; an electrocorticography (ECOG) device; a deep-brain stimulation device; or a magnetoencephalography (MEG) device.

4. The glucose management device of claim 1, wherein to decode the brain activity signal, the glucose monitoring application further directs the processor to provide the brain activity signal to a multivariate decoder trained on spectral profiles of intracranial activity.

5. The glucose management device of claim 1, wherein the brain activity signal describes the spectral profile of the broadband brain activity.

6. The glucose management device of claim 1, wherein the glucose monitoring application further directs the processor to deliver a therapy to the user based on the predicted future glucose levels in order to manage glucose levels in a desired therapeutic range.

7. The glucose management device of claim 6, wherein the therapy is insulin provided via an insulin pump to the user.

8. The glucose management device of claim 6, wherein the therapy is brain stimulation.

9. The glucose management device of claim 1, wherein the glucose monitoring application further directs the processor to: store the predicted future glucose levels in the memory; and validate the predicted future glucose levels based on a measured glucose level received from a glucose monitor.

10. The glucose management device of claim 1, wherein the glucose level is selected from the group consisting of: blood glucose level; or interstitial glucose level.

11. A method of managing glucose levels, comprising:
recording a brain activity signal of a user's brain using a brain signal recorder; and
decoding the brain activity signal to predict future glucose levels of the user, wherein the brain activity signal is coherent to intracranial high frequency activity, and wherein the predicted future glucose levels comprise glucose levels predicted at least two hours in advance.

12. The method of managing glucose levels of claim 11, further comprising providing a warning when estimated glucose levels rise above a threshold value.

13. The method of managing glucose levels of claim 11, wherein the brain signal recorder is selected from the group consisting of: an electroencephalography (EEG) device; a functional near-infrared spectroscopy (fNIRS) device; an electrocorticography (ECOG) device; a deep-brain stimulation device; or a magnetoencephalography (MEG) device.

14. The method of managing glucose levels of claim 11, decoding the brain activity signal comprises providing the brain activity signal to a multivariate decoder trained on spectral profiles of intracranial activity.

15. The method of managing glucose levels of claim 11, wherein the brain activity signal describes the spectral profile of the broadband brain activity.

16. The method of managing glucose levels of claim 11, further comprising delivering a therapy to the user based on the predicted future glucose levels in order to manage glucose levels in a desired therapeutic range.

17. The method of managing glucose levels of claim 16, wherein the therapy is insulin provided via an insulin pump to the user.

18. The method of managing glucose levels of claim 16, wherein the therapy is brain stimulation.

19. The method of managing glucose levels of claim 11, further comprising: storing the predicted future glucose levels in the memory; and validating the predicted future glucose levels based on a measured glucose level received from a glucose monitor.

20. The method of managing glucose levels of claim 11, wherein the glucose level is selected from the group consisting of: blood glucose level; or interstitial glucose level.

* * * * *